United States Patent [19]

Binnig et al.

[11] 4,010,282
[45] Mar. 1, 1977

[54] ANTI-ARRHYTHMIC AGENTS

[75] Inventors: Fritz Binnig, Fussgoennheim; Manfred Raschack, Weisenheim am Sand, both of Germany

[73] Assignee: Knoll A.G. Chemische Fabriken, Ludwigshafen (Rhine), Germany

[22] Filed: June 25, 1975

[21] Appl. No.: 590,156

[30] Foreign Application Priority Data

Aug. 9, 1974 Germany .................... 2438288

[52] U.S. Cl. ............................................. 424/330
[51] Int. Cl.$^2$ ..................................... A61K 31/135
[58] Field of Search .................................. 424/330

[56] References Cited

OTHER PUBLICATIONS

J. Med. Chem., 9(3), 329–334, (1966).
J. Med. Chem., 7(4), 500–503, (1964); vol. 8(3), (1965), 401–404.

*Primary Examiner*—Frederick E. Waddell
*Attorney, Agent, or Firm*—Curtis, Morris & Safford

[57] ABSTRACT

Methods of treating cardiac arrhythmia by the oral or parenteral administration of N,N'-dibenzyl-alkylene diamine compounds of the formula

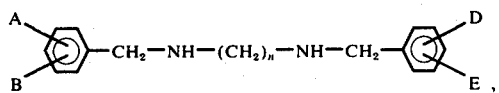

or salts thereof with pharmaceutically acceptable acids, wherein A, B, D, and E are hydrogen, chlorine, or methoxy, and $n$ is 2, 3, or 4; therapeutic compositions containing these anti-arrhythmic agents in combination with a pharmaceutical excipient.

3 Claims, No Drawings

ANTI-ARRHYTHMIC AGENTS

The present invention relates to methods for treating arrhythmia with N,N'-dibenzyl alkylene diamines and to therapeutic compositions containing such compounds as an active ingredient.

The anti-arrhythmic agents heretofore used in therapy are accompanied by side effects, such as a negative influence on the contractile force of the heart, so that the use of these preparations is not without problems and involves a certain weighing of risks [cf., for example, Muertz et al., Med. Mschr. 24, 239–245 (1970) and Bleifeld et al., Dtsch. Med. Wschr. 96, 671–680 (1971)]. Thus, it is desirable to develop anti-arrhythmic agents which have a larger margin of safety between a dose which has an anti-arrhythmic effect and a dose having a negative inotropic effect, i.e., to develop agents which exhibit a greater therapeutic breadth than, for example, the well known substances such as antazoline, lidocaine, or N-propylajmaline.

It has now been found that certain alkylene diamine compounds which have not heretofore been used therapeutically are suitable for the treatment of disturbances of cardiac function.

The present invention relates more in particular to therapeutic agents which contain alkylene diamine compounds of the formula:

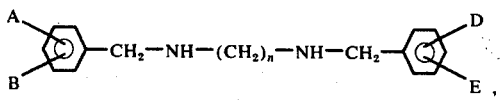

wherein A, B, D, and E are the same or different and are hydrogen, chlorine, or methoxy, and wherein $n$ is 2, 3, or 4, or their salts with physiologically-tolerable acids.

As physiologically-tolerable acids, materials such as hydrochloric acid, sulfuric acid, phosphoric acid, acetic acid, malonic acid, succinic acid, maleic acid, citric acid, tartaric acid, lactic acid, and diamido sulfonic acid are exemplary.

The alkylene diamine derivatives, which for the most part are known in the art, can be prepared by reacting an α,ω-dihaloalkane with benzylamine, which latter may be substituted, or by reacting an α,ω-diaminoalkane with benzyl chloride, which may be substituted, or by reducing an α,ω-di-(benzylideneamino)-alkane, which latter may also be substituted in the benzene rings.

The reaction of the amines with the halides can take place in the conventional manner in the presence or absence of a solvent. Suitable solvents are, for example, inert hydrocarbons. It is particularly advantageous to use an excess of the amine component as the solvent.

The reaction can be carried out at temperatures from about 40° to about 250° C., preferably between 70° and 140° C. The isolation of the reaction product suitably follows by distillation. It is recommended to convert the free bases so obtained into their salts which, in case it is necessary, can be further purified by recrystallization.

The reduction of dibenzylidene compounds can take place with the usual reducing agents such as platinum/hydrogen, lithium aluminum hydride, or sodium borohydride.

The evidence of the anti-arrhythmic effect of the new compounds can be demonstrated on experimental animals by determination of the functional refractory period of the left auricle of the guinea pig using paired electrical stimulation according to the method of W. C. Jovier, J. Pharmakol. Exp. Therap. 148, 100–105 (1965). In this experimental arrangement, the numerous anti-arrhythmic agents, of different chemical structure and different therapeutic points of attack in man, heretofore used in therapy are all characterized by a lengthening of the functional refractory period. The method additionally permits determining the effects of the substance on the contractile force of the heart muscle [Reuter and Heeg, Naunyn-Schmiedeberg's Arch. Pharmak. 268, 323–333 (1971) and Zetler and Strubelt, Naunyn-Schmiedeberg's Arch. Pharmak. 271, 335–345 (1971)]. It is, thus, highly suitable for detecting substances having a large therapeutic breadth, i.e., with a large margin of safety between anti-arrhythmically- and negative inotropically-effective doses.

The testing of the substances employed up to 30 individual experiments in each case. For the determination of the effective dose, linear regression functions were calculated [cf. A. Lindner, Statistische Methoden, 3rd Edition, Birkhaeuser Verlag, Basel (1969)], in which the maximum percentage deviations from the starting value in a time period up to 30 minutes after addition of the test substance to the bath liquid was employed.

In column I of following Table 1, one of the new compounds and known anti-arrhythmic agents are entered. Column II gives the anti-arrhythmic effect. Column III reports the inotropic effect. The therapeutic breadth of the compounds is given in column IV. The $ED_{25}$ is the effective dose which lengthens the refractory period by 25 percent or lowers the contractile force by 25 percent. It is evident from the Table that the substance of the invention is clearly superior to the known substances from the point of view of the safety margin between the desired rhythm-regularizing effect and the undesirable influence on the contractility of the heart.

TABLE I

| I<br>Anti-arrhythmic<br>Agent | II<br>Anti-arrhythmic Effect<br>(Prolongation of the<br>Refractory Period) | III<br>Inotropic Effect<br>(Decrease in<br>Contractile Force) | IV<br>Therapeutic Breadth<br>(III/II) |
|---|---|---|---|
| N,N'-dibenzyl-propylene-diamine-1,3 | $ED_{25} = 0.054$ | $ED_{25} = 0.141$ | 2.6 |
| N,n-propylajmaline | $ED_{25} = 0.0037$ | $ED_{25} = 0.0015$ | 0.4 |
| Antazoline | $ED_{25} = 0.164$ | $ED_{25} = 0.094$ | 0.6 |

Table 2 summarizes the good anti-arrhythmic efficacy of the diamines of the invention. The N,N'-dibenzyl propylene diamine of Table 1 is also contained in Table 2.

TABLE 2

| | Dose Mol/l | Anti-arrhythmic Effect (% Prolongation of the Refractory Period) |
|---|---|---|
| N,N'-dibenzyl-propylenediamine | $10^{-4}$ | 47 |
| N,N'-dibenzyl-ethylenediamine | $10^{-4}$ | 39 |
| N,N'-dibenzyl-butylenediamine | $10^{-4}$ | 44 |
| N,N'-di-(m-chlorobenzyl)-propylenediamine | $2 \times 10^{-5}$ | 45 |
| N,N'-di-(p-chlorobenzyl)-propylenediamine | $10^{-5}$ | 37 |
| N,N'-di-(m,p-dichlorobenzyl)-propylenediamine | $10^{-5}$ | 26 |
| N,N'-di-(m-methoxybenzyl)propylenediamine | $5 \times 10^{-5}$ | 40 |
| N,N'-di-(p-methoxybenzyl)-propylenediamine | $10^{-4}$ | 51 |
| N,N'-di-(m,p-dimethoxybenzyl)propylenediamine | $10^{-4}$ | 42 |

The anti-arrhythmic effect of the diamines could also be confirmed in intact research animals with an experimentally-induced disturbance of the heart rhythm. If rats are continuously infused intravenously with aconitine, severe disturbances in the heartbeat sequence, such as extrasystoles, ventricular tachycardia, and ventricular flutter, which eventually lead to the death of the experimental animal, can be detected in an electrocardiogram. By a pre-treatment with the new pharmaceutical agents, the appearance of these threatening disturbances of the heart rhythm can be hindered or, on continuous administration of aconitine, can be considerably delayed. This experimental model of arrhythmia has already been checked for its evidentiary value using clinically tested standard therapeutic agents and is highly suitable for an experimental animal characterization of anti-arrhythmic agents [cf. Bianchi et al., Arzneim. Forsch. 18, 845–850 (1968); Haas and Busch, Arzneim. Forsch. 18, 401–407 (1968); Haas et al., Arzneim. Forsch. 21, 1392–1399 (1971); Marmo, Naunyn-Schmiedeberg's Arch. Pharmak. 269, 231–247 (1971); and Strubelt et al., Naunyn-Schmiedeberg's Arch. Pharmak. 271, 346–360 (1971)].

Table 3 shows the results of tests on N,N'-dibenzyl propylene diamine. The $ED_{25}$ and $ED_{50}$ are the intravenous or oral doses in mg/kg that permit a 25 percent or 50 percent increase in the dosage of aconitine administered, versus the aconitine control, until the occurrence of extrasystoles, ventricular tachycardia, and ventricular flutter.

This Table also shows the superior effect of the new pharmaceuticals, for example N,N'-dibenzyl propylene diamine-1,3, which can be administered parenterally as well as orally.

A better understanding of the present invention and of its many advantages will be had by referring to the following specific examples, given by way of illustration.

Preparation of the Compounds a. N,N'-di-(3'-chlorobenzyl)-propylene-1,3-diamine.

35.8 g of 1,3-dibromopropane are added dropwise to 100 g of 3-chlorobenzylamine with stirring at 90°–100° C. The mixture is then stirred for one hour at 130°–140° C. After cooling, a solution of 30 g of sodium hydroxide in 400 ml of water is added dropwise and then the mixture is extracted four times with 200 ml portions of diethyl ether. The ether extracts are dried over potassium hydroxide and concentrated. The residue is distilled in vacuum. At 166°–172° C., 0.05 mm Hg, 33.1 g of the desired compound distill over.

The compound so obtained is dissolved in isopropanol and, for salt formation, combined with a calculated amount of maleic acid. The isopropanol is distilled off and the residue, comprising N,N'-di-(3'-chlorobenzyl)-propylene-1,3-diamine-di-maleinate, is recrystallized from methanol/water. m.p. = 203°–204° C.

b. N,N'-di-(4'-chlorobenzyl)-1,3-diaminopropane.

A solution of 54.7 g of N,N'-di-(4-chlorobenzylidene)-1,3-diaminopropane in 1 liter of methanol is combined in an ice bath, with stirring, with 19.1 g of sodium borohydride. After addition of the hydride, the mixture is stirred for a further hour and then refluxed at the boiling point for an additional ½ hour.

After cooling, 1 liter of 10 percent sodium hydroxide is added, the mixture is shaken four times with 100 ml portions of diethyl ether, and the ether extracts are dried over sodium hydroxide. After distilling off the

TABLE 3

| | | N,N'-DIBENZYL-PROPYLENEDIAMINE-1,3 | | SPARTEINE |
|---|---|---|---|---|
| | | i.v. | p.o. | i.v. |
| Extrasystoles | $ED_{25}$ | 5.2 | 65.8 | +) |
| | $ED_{50}$ | 6.0 | 96.2 | +) |
| Ventr. Tachycardia | $ED_{25}$ | 5.3 | 55.4 | 4.4 |
| | $ED_{50}$ | 6.2 | 71.6 | 9.6 |
| Ventr. Flutter | $ED_{25}$ | 4.9 | 51.1 | +) |
| | $ED_{50}$ | 6.4 | 69.9 | +) |

+) no significant effect attainable

The alkylene diamine derivatives and their salts with physiologically-tolerable acids may be administered orally and parenterally. The dose for intravenous or intramuscular administration is about 0.1–2.0 mg/kg per day and about 1–10 mg/kg per day for oral use. For administration, the well known galenic dosage unit forms are suitable, such as tablets, drageés, capsules, and solutions.

ether, 47 g of a colorless oil are obtained by vacuum distillation at 180° C/0.01 mm Hg. The oil has an index of refraction $N_D^{25} = 1.5715$. The di-maleinate, prepared as in part (a), melts at 219°–220° C.

EXAMPLE 1

Tablets are prepared in a conventional manner in a tablet press from the following composition:

70.00 mg of N,N'-dibenzyl-propylene diamine-dihydrochloride
50.00 mg of corn starch
4.50 mg of gelatin
15.00 mg of lactose
7.50 mg of talc
0.75 mg of chemically pure submicroscopically-divided silicic acid ("Aerosil")
2.25 mg of potato starch (as a 6 percent paste).

EXAMPLE 2

Drageés of the following composition are prepared in the usual manner:
50.00 mg of N,N'-dibenzyl-propylene diamine
85.00 mg of corn mass
80.00 mg of sugaring mass The core mass comprises 9 parts of corn starch, 3 parts of lactose, and 1 part of a 60:40 vinyl pyrrolidone-vinyl acetate copolymer ("Luviscol VA 64"), cf. Pharm. Ind. 1962, 586. The sugaring mass comprises 5 parts of cane sugar, 2 parts of corn starch, 2 parts of calcium carbonate, and 1 part of talc. The dragees so prepared are subsequently coated with a coating resistant to stomach juices.

EXAMPLE 3

50 g of N,N'-dibenzyl-propylene diamine-di-maleinate are dissolved in 5 liters of water, isotonically adjusted with sodium chloride, and filled into ampules holding 5 ml.

What is claimed is:

1. The method of treating cardiac arrhythmia in a patient suffering therefrom which comprises orally or parenterally administrating a therapeutically effective amount of an N,N'-dibenzyl alkylene diamine compound of the formula

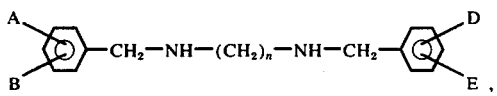

or of a salt thereof with a physiologically tolerable acid, wherein A, B, D, and E are hydrogen, chlorine, or methoxy, and $n$ is 2, 3, or 4.

2. The method as in claim 1 wherein from 0.1–2.0 mg/kg/day of said compound or salt are parenterally administered.

3. The method as in claim 1 wherein from 1–10 mg/kg/day of said compound or salt are administered orally.